United States Patent [19]

Nüsslein et al.

[11] 4,378,318
[45] Mar. 29, 1983

[54] CARBANILIC ACID-(3-UREIDO-PHENYL)-ESTERS

[75] Inventors: Ludwig Nüsslein; Friedrich Arndt, both of Berlin, Fed. Rep. of Germany

[73] Assignee: Schering Aktiengesellschaft, Berlin and Bergkamen, Fed. Rep. of Germany

[21] Appl. No.: 283,667

[22] Filed: Jul. 15, 1981

Related U.S. Application Data

[63] Continuation of Ser. No. 109,687, Jan. 4, 1980, abandoned, which is a continuation of Ser. No. 921,106, Jun. 30, 1978, abandoned.

[30] Foreign Application Priority Data

Jan. 7, 1977 [DE] Fed. Rep. of Germany ....... 2730325

[51] Int. Cl.$^3$ .......................................... C07C 127/19
[52] U.S. Cl. .................................. 260/465 D; 71/104; 71/111; 560/9; 560/29
[58] Field of Search ................. 260/465 D; 560/29, 9; 71/111

[56] References Cited

U.S. PATENT DOCUMENTS

| | | | |
|---|---|---|---|
| 3,133,808 | 5/1964 | Hamm | 71/118 |
| 3,284,487 | 11/1966 | von Brachel | 71/111 |
| 3,404,975 | 10/1968 | Wilson et al. | 560/29 |
| 3,778,473 | 12/1973 | Kornis et al. | 71/111 |
| 3,780,104 | 12/1973 | Leach | 71/100 |
| 3,806,537 | 4/1974 | Dorscher et al. | 71/100 |
| 3,867,426 | 2/1975 | Olin et al. | 71/111 |
| 3,879,441 | 5/1975 | Boroschewski et al. | 71/111 |
| 3,920,727 | 11/1975 | Metzger et al. | 560/29 |
| 4,067,726 | 1/1978 | Sasse et al. | 71/111 |

Primary Examiner—Dolph H. Torrence
Attorney, Agent, or Firm—Michael J. Striker

[57] ABSTRACT

Herbicidal compositions comprising or consisting of a compound of the formula

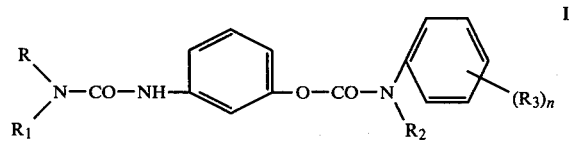

in which R is an aliphatic, straight chain, branched or cyclic, saturated or unsaturated hydrocarbon residue of 1 to 6 carbons, $R_1$ is hydrogen or methyl, $R_2$ is cyanoalkyl or alkoxyalkyl, $R_3$ is the same or different if more than one and is hydrogen, alkyl, alkoxy, alkylthio or halogen and n is 1 or 2. The compounds have a broad soil and leaf herbicidal effect and are suited particularly for selective weed suppression in cultures like soybeans, peas, alfalfa, potatoes, maize, sorghum, rice, wheat and barley.

10 Claims, No Drawings

CARBANILIC ACID-(3-UREIDO-PHENYL)-ESTERS

This is a continuation, of application Ser. No. 109,687, filed Jan. 4, 1980, abandoned, which is in turn a continuation of application of application Ser. No. 921,106 filed June 30, 1978, abandoned.

BACKGROUND OF THE INVENTION

The invention relates to new carbanilic acid-(3-ureido-phenyl)-esters.

N-carbamoyloxyphenyl-urea derivatives are known as herbicides (German published application No. 1 518 815), for instance N-(3-N-tert.-butylcarbamoyloxy)-phenyl)-N'',N''-dimethylurea. Compounds of this kind, however, are useful only for total destruction of a flora, but not for the selective weed suppression in important agricultural areas.

An object of the invention is therefore the provision of an agent which has a superior activity against weeds and at the same time has a broad selectivity spectrum towards important agricultural plants.

SUMMARY OF THE INVENTION

This object is met by a herbicidal composition comprising or consisting of a compound of the formula

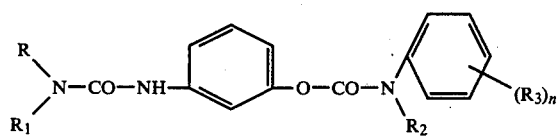

in which R is an aliphatic, straight chain, branched or cyclic, saturated or unsaturated hydrocarbon residue of 1 to 6 carbons, $R_1$ is hydrogen or methyl, $R_2$ is cyanoalkyl or alkoxyalkyl, $R_3$ is the same or different if more than 1 and is hydrogen, alkyl, alkoxy, alkylthio or halogen and n is 1 or 2.

DESCRIPTION OF PREFERRED EMBODIMENTS

The hydrocarbon residue above indicated as R is preferably $C_1$–$C_6$-alkyl, e.g. methyl, ethyl, propyl, isopropyl, butyl, isobutyl, sec.-butyl, tert.-butyl, pentyl, isopentyl, hexyl, propinyl, cyclopropyl or cyclohexyl. The group identified as $R_2$ preferably is cyanomethyl, 2-cyanoethyl or 2-methoxyethyl, 2,2-dimethoxyethyl, 2-ethoxyethyl, 2-propoxyethyl or 2-butoxyethyl. $R_3$ preferably is hydrogen, methyl, methoxy, methylthio and/or chlorine.

The compounds of the invention are characterized by a broad activity when applied to the soil or leaves. They can be used to suppress monocotyl and dicotyl weeds. Particularly useful are the compounds against dicotyl and monocotyl weeds of the families Portulaca, Papaver, Kochia, Gypsophyla, Solanum, Escholtzia, Cheiranthus, Phacelia, Brassica, Datura, Ipomea, Agrostis, Alopecurus, Stellaria, Senecio, Matricaria, Lamium, Centaurea, Amaranthus, Chrysanthemum, Polygonum, Setaria, Poa and others.

The amounts to be used for the selective weed suppression are between 0.5 and 5 kg of active agent per about 2.5 acres.

The selective weed control is possible in cultures such as soybeans, peas, alfalfa, potatoes, maize, sorghum, rice, wheat and barley.

The highest activity have these compounds if they are sprayed onto the just emerging weed and cultures.

The compounds of the invention can either be used singly or intermixed with each others or in mixture with other active agents. To bridge any activity gaps the addition of other active agents is particularly useful. Such agents are, for instance:
substituted anilines,
substituted aryloxycarboxylic acids and their salts, esters and amides,
substituted ethers,
substituted arsonic acids and their salts, esters and amides,
substituted benzimidazoles,
substituted benzthiadiazinone dioxides,
substituted benzoxazines,
substituted benzoxazinones,
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkyl-thio- or dithiophosphates
substituted quinazolines,
substituted cycloalkylamidocarbonylthiol acids and their salts, esters and amides,
substituted cycloalkylcarboxylamido-thiazoles,
substituted dicarboxylic acids and their salts, esters and amides,
substituted dihydrobenzofuranylsulfonates,
substituted disulfides,
substituted dipyridylium salts,
substituted dithiocarbamates,
substituted dithiophosphoric acids and their salts, esters and amides,
substituted urea derivatives,
substituted hexahydro-1H-carbothioates,
substituted hydantoines,
substituted hydrazides,
substituted hydrazonium salts,
substituted isoxazolpyrimidones,
substituted imidazoles,
substituted isothiazolpyrimidones,
substituted ketones,
substituted naphthoquinones,
substituted aliphatic nitriles,
substituted aromatic nitriles,
substituted oxadiazoles,
substituted oxadiazinons,
substituted oxadiazolidinediones,
substituted oxadiazinediones,
substituted phenols and their salts and esters,
substituted phosphonic acids and their salts, esters and amides,
substituted phosphoniumchlorides,
substituted phosphonalkylglycines,
substituted phosphites,
substituted phosphoric acids and their salts, esters and amides,
substituted piperidines,
substituted pyrazoles,
substituted pyrazolalkylcarboxylic acids and their salts, esters, and amides, substituted pyrazolium salts,
substituted pyrazoliumalkylsulfates,
substituted pyridazines,
substituted pyridazones,
substituted pyridine-carboxylic acids and their salts, esters and amides,
substituted pyridines,
substituted pyridinecarboxylates,
substituted pyridinones,
substituted pyrimidones,
substituted pyrrolidine-carboxylic acids and their salts, esters and amides,
substituted pyrrolidines,
substituted pyrrolidones,
substituted arylsulfonic acids and their salts, esters and amides,
substituted styrenes,
substituted tetrahydro-oxadiazindiones,
substituted tetrahydromethanoindenes,
substituted tetrahydro-diazol-thiones,
substituted tetrahydro-thiadiazine-thiones,
substituted tetrahydro-thiadiazolediones,
substituted thiadiazoles,
substituted aromatic thiocarboxylic acid amides,
substituted thiocarboxylic acids and their salts, esters and amides,
substituted thiolcarbamates,
substituted thiourea derivatives,
substituted thiophosphoric acids and their salts, esters and amides,
substituted triazines,
substituted triazoles,
substituted uracils, and
substituted urethidindiones.

The added agents may be incorporated in the compositions also immediately prior to application.

It is possible also to use other additives such as non-phytotoxic additives which in herbicides have a synergistic increase of the activity such as wetting agents, emulsifiers, solvents and oily additives.

Preferably, the compounds of the invention or their mixtures are used in the form of compositions such as powders, dusting agents, granulates, emulsions or suspensions. Liquid and/or solid carrier materials or diluents are added and there may also be added wetting agents, adhesion promoting agents, emulsifiers and/or dispersants.

Suitable liquid carrier materials are for instance water, aliphatic and aromatic hydrocarbons such as benzene, toluene, xylene, cyclohexanone, isophorone, dimethylsulfoxide, and furthermore mineral oil fractions.

As solid carrier materials there are suitable mineral earths, for instance, tonsil, silicagel, talc, kaolin, attaclay, limestone and plant products, for instance flours.

There may be added surface active agents such as calciumlignosulfonate, polyoxyethylenealkyl-phenylether, naphthalenesulfonic acids and their salts, phenolsulfonic acids and their salts, formaldehyde condensation products, fatty alcohol sulfates as well as substituted benzene sulfonic acids and their salts.

The proportions of the active agents in the different solutions can be varied widely. For instance, the compositions may contain about 10 to 80% by weight of active agents, about 90 to 20% by weight of liquid or solid carrier materials and, if desired, up to 20% by weight of surface active agents in which case a corresponding reduction of the carrier materials is effected.

The application of the compositions can be carried out in conventional form, for instance with water as the carrier material in spray amounts of about 100 to 1000 liters per about 2.5 acres. An application of the compositions is possible in the so-called "low volume" and "ultra low volume process" as well as in the form of so-called microgranulates.

PROCESS OF MAKING THE COMPOUNDS

The compounds of the invention can be made in various ways.

I. 1-(3-hydroxyphenyl)-3-alkylurea derivatives of the formula 1-(3-hydroxyphenyl)-3-alkylurea derivatives of the formula

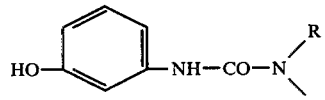

can be reacted with (a) in the presence of acid acceptors with carbanilic acid chlorides of the formula

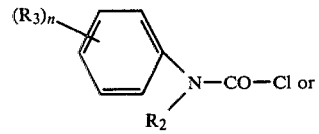

(b) with phosgene

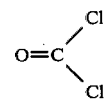

likewise in the presence of acid acceptors so as to form chloroformic acid-[3-(3-alkylureido)-phenyl]-ester of the formula

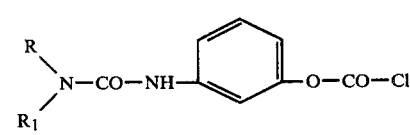

followed by reaction with amines of the formula

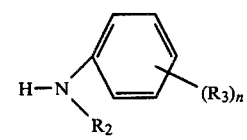

II. Carbanilic acid-(3-nitrophenyl)-ester of the formula

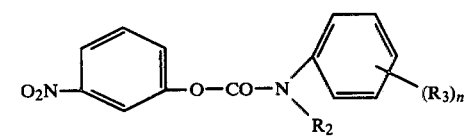

may be hydrogenated to the corresponding amines in the presence of a catalyst, preferably Raney nickel. Where $R_1$ is methyl the corresponding amines are then reacted with carbamic acid chloride of the formula

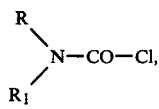

Where $R_1$ is hydrogen the amine is reacted with an isocyanate of the formula

R—N=C=O.

In all of the above formulas R, $R_1$, $R_2$, $R_3$ and n have the meaning as in the above formula I.

Acid acceptors in these reactions may be the compounds conventionally used for this purpose. Suited are for instance organic bases such as tertiary amines, for instance triethylamine or N,N-dimethylaniline or pyridine bases. Suitable inorganic bases are, for instance, oxides, hydroxides and carbonates of the alkali metals and alkali earth metals. If liquid organic bases are used they may serve simultaneously as solvents.

The reactions between the components should be carried out at a temperature between 0° and 120° C., preferably at a medium temperature between these limits. The reactants preferably are used in equimolar amounts.

Suitable reaction media are solvents which are insert towards the reactants. As such may be named: aliphatic and aromatic hydrocarbons, such as, petrol ether, cyclohexane, benzene, toluene and xylene; halogenated hydrocarbons, such as, methylenechloride, chloroform, carbontetrachloride and halogenated ethylenes; ether-like compounds, such as, diethylether, tetrahydrofuran and dioxane; ketones, such as acetone, methylisobutylketone and isophorone; ester, such as acetic acid methyl- and ethylester, acid amides, such as dimethylformamide and hexamethylphosphoric acid triamide, carboxylic acid nitriles, such as acetonitrile, and many others.

The isolation of the formed compounds of the invention in case of compounds of low solubility is effected by filtration. If the compounds have a better solubility it may be effected by distilling off the solvent at atmospheric or reduced pressure or by precipitation either with water or with non-polar organic solvents such as hydrocarbons or ethers and others.

The following examples will further illustrate the making of the compounds of the invention:

EXAMPLE 1

16.6 g of 1-(3-hydroxyphenyl)-3-methyl urea having a melting point of 130° C. were added to a solution of 6.58 g of 85% potassium hydroxide in 100 ml methanol followed by distilling off the solvent in a vacuum. The residue was then suspended in 200 ml acetonitrile and thereafter was reacted with 21 g of N-(2-cyanoethyl)-carbanilic acid chloride. The reaction mixture was then heated to boiling point for 1 hour and after cooling off was added upon stirring to 1 liter of icewater. The precipitated compound was removed by suction, dried and recrystallized from methylisobutylketone.

There were obtained 25 g (74% of the calculated value) of N-(2-cyanoethyl)-carbanilic acid-[3-(3-methylureido)phenyl]-ester having a melting point of 147° C.

In an analogous manner the following compounds of the invention were obtained:

| Compound of the invention | Physical constants |
|---|---|
| N—(2-cyanoethyl)-carbanilic acid-[3-(3-cyclopropylureido)-phenyl]-ester | m.p.: 104° C. |
| N—(2-cyanoethyl)-carbanilic acid-[3-(3,3-dimethylureido)-phenyl]-ester | m.p.: 142° C. |
| N—(2-cyanoethyl)-carbanilic acid-[3-(3-propylureido)-phenyl]-ester | m.p.: 131° C. |
| N—(2-cyanoethyl)-carbanilic acid-[3-[3-(2-propenyl)-ureido]-phenyl]-ester | m.p.: 113° C. |
| N—(2-cyanoethyl)-carbanilic acid-[3-(3-butylureido)-phenyl]-ester | m.p.: 88° C. |
| N—(2-cyanoethyl)-carbanilic acid-[3-(3-isopropylureido)-phenyl]-ester | m.p.: 136° C. |
| N—(2-cyanoethyl)-3-methylcarbanilic acid-[3-(3-isopropylureido)-phenyl]-ester | m.p.: 182° C. |
| N—(2-cyanoethyl)-3-methylcarbanilic acid-[3-(3-propylureido)-phenyl]-ester | m.p.: 125° C. |
| N—(2-cyanoethyl)-3-methylcarbanilic acid-[3-(3-ethylureido)-phenyl]-ester | m.p.: 159° C. |
| N—(2-cyanoethyl)-3-methylcarbanilic acid-[3-(3-methylureido)-phenyl]-ester | m.p.: 162° C. |
| N—(2-cyanoethyl)-3-methylcarbanilic acid-[3-(3-cyclopropylureido)-phenyl]-ester | m.p.: 143° C. |
| N—(2-cyanoethyl)-3-methoxycarbanilic acid-[3-(3-isopropylureido)-phenyl]-ester | m.p.: 147° C. |
| N—(2-cyanoethyl)-3-methoxycarbanilic acid-[3-(3-methylureido)-phenyl]-ester | m.p.: 125° C. |
| N—(2-cyanoethyl)-3-methoxycarbanilic acid-[3-(3-cyclopropylureido)-phenyl]-ester | m.p.: 120° C. |
| N—(2-cyanoethyl)-3-methylcarbanilic acid-[3-(3-butylureido)-phenyl]-ester | m.p.: 106° C. |
| N—(2-cyanoethyl)-3-methoxycarbanilic acid-[3-(3-ethylureido)-phenyl]-ester | m.p.: 121° C. |
| N—(2-cyanoethyl)-3-methylcarbanilic acid-[3-(3,3-dimethylureido)-phenyl]-ester | m.p.: 116° C. |
| N—cyanomethyl-carbanilic acid-[3-(3,3-dimethylureido)-phenyl]-ester | m.p.: 183° C. |
| N—(2-cyanoethyl)-3-methoxycarbanilic acid-[3-(3,3-dimethylureido)-phenyl]-ester | m.p.: 96° C. |
| N—Cyanomethyl-carbanilic acid-[3-(3-ethylureido)-phenyl]-ester | m.p.: 159° C. |
| N—cyanomethyl-carbanilic acid-[3-(3-isopropylureido)-phenyl]-ester | m.p.: 178° C. |
| N—(2-cyanoethyl)-3-methylcarbanilic acid-[3-(3-allylureido)-phenyl]-ester | m.p.: 124° C. |
| N—(2-cyanoethyl)-3-methoxycarbanilic acid-[3-(3-propylureido)-phenyl]-ester | m.p.: 124° C. |
| N—cyanomethyl-carbanilic acid-[3-(3-methylureido)-phenyl]-ester | m.p.: 144° C. |
| N—cyanomethyl-3-methylcarbanilic acid-[3-(3-ethylureido)-phenyl]-ester | m.p.: 122° C. |
| N—cyanomethylcarbanilic acid-[3-(3-propylureido)-phenyl]-ester | m.p.: 156° C. |
| N—cyanomethylcarbanilic acid-[3-(3-cyclocyclopropylureido)-phenyl]-ester | m.p.: 172° C. |
| N—cyanomethylcarbanilic acid-[3-(3-butylureido)-phenyl]-ester | m.p.: 110° C. |
| N—cyanomethylcarbanilic acid-[3-(3-allylureido)-phenyl]-ester | m.p.: 130° C. |
| N—cyanomethyl-3-methylcarbanilic acid-[3-(3,3-dimethylureido)-phenyl]-ester | m.p.: 145° C. |
| N—cyanomethyl-3-methylcarbanilic acid-[3-(3-isopropylureido)-phenyl]-ester | m.p.: 122° C. |
| N—cyanomethyl-3-methylcarbanilic acid-[3-(3-methylureido)-phenyl]-ester | m.p.: 162° C. |
| N—cyanomethyl-3-methylcarbanilic acid-[3-(3-propylureido)-phenyl]-ester | m.p.: 119° C. |
| 3-chloro-N—cyanomethyl-carbanilic acid-[3-(3,3-dimethylureido)-phenyl]-ester | m.p.: 146° C. |
| N—cyanomethyl-3,4-dichloro-carbanilic acid-[3-(3,3-dimethylureido)-phenyl]-ester | m.p.: 150° C. |
| N—cyanomethyl-3-chloro-carbanilic acid-[3-(3-ethylureido)-phenyl]-ester | m.p.: 141° C. |
| N—cyanomethyl-3-methoxycarbanilic acid-[3-(3,3-dimethylureido)-phenyl]-ester | m.p.: 152° C. |

-continued

| Compound of the invention | Physical constants |
|---|---|
| 3-chloro-N—cyanomethyl-carbanilic acid-[3-(3-propylureido)-phenyl]-ester | m.p.: 126° C. |
| N—cyanomethyl-3-methylcarbanilic acid-[3-(3-allylureido)-phenyl]-ester | m.p.: 100° C. |
| N—cyanomethyl-3-methoxycarbanilic acid-[3-(3-methylureido)-phenyl]-ester | m.p.: 123° C. |
| N—cyanomethyl-3-methoxycarbanilic acid-[3-(3-propylureido)-phenyl]-ester | m.p.: 125° C. |
| N—cyanomethyl-3-methoxycarbanilic acid-[3-(3-allylureido)-phenyl]-ester | m.p.: 87° C. |
| 3-chloro-N—cyanomethyl-4-methylcarbanilic acid-[-(3-methylureido)-phenyl]-ester | m.p.: 135° C. |
| 3-chloro-N—cyanomethyl-4-methylcarbanilic acid-[3-(3,3-dimethylureido)-phenyl]-ester | m.p.: 179° C. |
| N—cyanomethyl-3-methoxycarbanilic acid-[3-(3-ethylureido)-phenyl]-ester | m.p.: 115° C. |
| N—(2-methoxyethyl)-3-methyl-carbanilic acid-[3-(3,3-dimethylureido)-phenyl]-ester | m.p.: 109° C. |
| 3-chloro-N—cyanomethyl-carbanilic acid-[3-(3-allylureido)-phenyl]-ester | m.p.: 125° C. |
| 3-chloro-N—cyanomethyl-4-methylcarbanilic acid-[3-(3-ethylureido)-phenyl]-ester | m.p.: 130° C. |
| N—cyanomethyl-3,5-dimethylcarbanilic acid-[3-(3-methylureido)-phenyl]-ester | m.p.: 116° C. |
| N—cyanomethyl-4-methylthio-carbanilic acid-[3-(3-methylureido)-phenyl]-ester | m.p.: 167° C. |
| N—cyanomethyl-3,5-dimethylcarbanilic acid-[3-(3,3-dimethylureido)-phenyl]-ester | m.p.: 146° C. |
| N—cyanomethyl-4-methylthio-carbanilic acid-[3-(3,3-dimethylureido)-phenyl]-ester | m.p.: 183° C. |
| N—cyanomethyl-3,5-dimethylcarbanilic acid-[3-(3-ethylureido)-phenyl]-ester | m.p.: 138° C. |
| N—cyanomethyl-4-methylthio-carbanilic acid-[3-(3-ethylureido)-phenyl]-ester | m.p.: 161° C. |
| N—cyanomethyl-3,5-dimethylcarbanilic acid-[3-(3-allylureido)-phenyl]-ester | m.p.: 110° C. |
| N—cyanomethyl-4-methylthio-carbanilic acid-[3-(3-allylureido)-phenyl]-ester | m.p.: 148° C. |
| N—cyanomethyl-3,4-dimethyl-carbanilic acid-[3-(3-methylureido)-phenyl]-ester | m.p.: 128° C. |
| N—cyanomethyl-3,4-dimethylcarbanilic acid-[3-(3-ethylureido)-phenyl]-ester | m.p.: 128° C. |
| N—cyanomethyl-3,4-dimethyl-carbanilic acid-[3-(3-allylureido)-phenyl]-ester | m.p.: 110° C. |
| 3,4-dichloro-N—cyanomethyl-carbanilic acid-[3-(3-ethylureido)-phenyl]-ester | m.p.: 139° C. |
| N—(2-methoxyethyl)-3-methyl-carbanilic acid-[3-(3-methylureido)-phenyl]-ester | m.p.: 101° C. |
| N—(2-methoxyethyl)-3-methyl-carbanilic acid-[3-(3-ethylureido)-phenyl]-ester | m.p.: 58° C. |
| 3,5-dimethyl-N—(2-methoxyethyl)-carbanilic acid-[3-(3,3-dimethylureido)-phenyl]-ester | m.p.: 142° C. |
| N—cyanomethyl-3,4-dimethylcarbanilic acid-[3-(3,5-dimethylureido)-phenyl]-ester | m.p.: 170° C. |
| N—cyanomethyl-3,5-dichlorocarbanilic acid-[3-(3-methylureido)-phenyl]-ester | m.p.: 131° C. |
| N—cyanomethyl-3,4-dichloro-carbanilic acid-[3-(3-methylureido)-phenyl]-ester | m.p.: 120° C. |
| N—(2-methoxyethyl)-carbanilic acid-[3-(3,3-dimethylureido)-phenyl]-ester | m.p.: 109° C. |
| N—cyanomethyl-3,5-dichlorocarbanilic acid-[3-(3,3-dimethylureido)-phenyl]-ester | m.p.: 163–165° C. |
| N—(2,2-dimethoxyethyl)-carbanilic acid-[3-(3,3-dimethylureido)-phenyl]-ester | oil |
| N—(2,2-dimethoxyethyl)-carbanilic acid-[3-(3-methylureido)-phenyl]-ester | oil |
| N—(2,2-dimethoxyethyl)-carbanilic acid-[3-(3-ethylureido)-phenyl]-ester | oil |
| N—(2,2-dimethoxyethyl)-carbanilic acid-[3-(3-isopropylureido)-phenyl]-ester | oil |
| N—(2-butoxyethyl)-carbanilic acid-[3-(3-methylureido)-phenyl]-ester | m.p.: 71° C. |
| N—(2-butoxyethyl)-carbanilic acid-[3-(3-ethylureido)-phenyl]-ester | m.p.: 85° C. |
| N—(2-cyanoethyl)-3-methylcarbanilic acid-[3-(3-sec-butylureido)-phenyl]-ester | m.p.: 128° C. |
| N—(2-butoxyethyl)-carbanilic acid-[3-(3,3-dimethylureido)-phenyl]-ester | m.p.: 80° C. |
| N—(2-butoxyethyl)-carbanilic acid-[3-(3-propylureido)-phenyl]-ester | m.p.: 73° C. |
| N—(2-ethoxyethyl)-carbanilic acid-[3-(3,3-dimethylureido)-phenyl]-ester | m.p.: 14° C. |
| N—(2-propoxyethyl)-carbanilic acid-[3-(3,3-dimethylureido)-phenyl]-ester | m.p.: 102° C. |

The compounds of the invention constitute colorless nonsmelling crystalline bodies which are insoluble in water but have increasing solubility in inorganic solvents in the following sequence: hydrocarbons, halogenated hydrocarbons, ethers, ketones, alcohols, carboxylic acids, carboxylic acid esters and carboxylic acid amides.

USES AND APPLICATIONS

The following examples will illustrate the application and activity of the compounds of the invention:

EXAMPLE 2

The compounds listed in the following Table 1 were applied in a hothouse in amounts of 5 kg of active agent per about 2.5 acres dissolved in 600 liters of water per 2.5 acres to the two test plants indicated in the table. The application was effected by spraying both in preemergence and postemergence application.

The results were evaluated three weeks after treatment on a scale in which 0=no effect and 4=total destruction of the plants.

As appears from the table there was normally obtained a complete destruction of the test plants.

TABLE I

| Compound of the invention | Preemergence | | Postemergence | |
|---|---|---|---|---|
|  | Sinapis | Solanum | Sinapis | Solanum |
| N—(2-cyanoethyl)-carbanilic acid-(3-(3,3-dimethylureido)-phenyl)-ester | 4 | 4 | 4 | 4 |
| N—(2-cyanoethyl)-carbanilic acid-(3-(3-methylureido)-phenyl)-ester | 4 | 4 | 4 | 4 |
| N—(2-cyanoethyl)-carbanilic acid-(3-(3-propylureido)-phenyl)-ester | — | — | 4 | 4 |
| N—(2-cyanoethyl)-carbanilic acid-(3-(3-(2-propenyl)-ureido)-phenyl)-ester | 4 | 4 | 4 | 4 |
| N—(2-cyanoethyl)-carbanilic acid-(3-(3-butylureido)-phenyl)-ester | — | — | 4 | 4 |
| N—(2-cyanoethyl)-carbanilic acid-(3-(3-isopropylureido)-phenyl)-ester | 4 | 4 | 4 | 4 |
| N—(2-cyanoethyl)-3-methylcarbanilic acid-(3-(3-isopropylureido)-phenyl)-ester | 4 | 4 | 4 | 4 |
| N—(2-cyanoethyl)-3-methylcarbanilic acid-(3-(3-propylureido)-phenyl)-ester | — | — | 4 | 4 |

TABLE I-continued

| Compound of the invention | Preemergence Sinapis | Preemergence Solanum | Postemergence Sinapis | Postemergence Solanum |
|---|---|---|---|---|
| N—(2-cyanoethyl)-3-methylcarbanilic acid-(3-(3-methylureido)-phenyl)-ester | — | — | 4 | 4 |
| N—(2-cyanoethyl)-3-methylcarbanilic acid-(3-(3-cyclopropylureido)-phenyl)-ester | — | — | 4 | 4 |
| N—(2-cyanoethyl)-3-methoxycarbanilic acid-(3-(3-isopropylureido)-phenyl)-ester | — | — | 4 | 4 |
| N—(2-cyanoethyl)-3-methylcarbanilic acid-(3-(3-ethylureido)-phenyl)-ester | — | — | 4 | 4 |
| N—(2-cyanoethyl)-3-methoxycarbanilic acid-(3-(3-methylureido)-phenyl)-ester | — | — | 4 | 4 |
| N—(2-cyanoethyl)-3-methoxycarbanilic acid-(3-(3-cyclopropylureido)-phenyl)-ester | — | — | 4 | 4 |
| N—(2-cyanoethyl)-3-methylcarbanilic acid-(3-(3-butylureido)-phenyl)-ester | — | — | 4 | 4 |
| N—(2-cyanoethyl)-3-methoxycarbanilic acid-(3-(3-ethylureido)-phenyl-ester | 4 | 4 | 4 | 4 |
| N—(2-cyanoethyl)-3-methylcarbanilic acid-(3-(3,3-dimethylureido)-phenyl)-ester | 4 | 4 | 4 | 4 |
| N—cyanomethyl-carbanilic acid-(3-(3,3-dimethylureido)-phenyl)-ester | 4 | 4 | 4 | 4 |
| N—(2-cyanoethyl)-3-methoxycarbanilic acid-(3-(3,3-dimethylureido)-phenyl)-ester | 4 | 4 | 4 | 4 |
| N—cyanomethyl-carbanilic acid-(3-(3-ethylureido)-phenyl)-ester | 4 | 4 | 4 | 4 |
| N—cyanomethyl-carbanilic acid-(3-(3-isopropylureido)-phenyl)-ester | 4 | 4 | 4 | 4 |
| N—(2-cyanoethyl)-3-methoxycarbanilic acid-(3-(3-propylureido)-phenyl)-ester | 4 | 4 | 4 | 4 |
| N—cyanomethyl-carbanilic acid-(3-(3-methylureido)-phenyl)-ester | 4 | 4 | 4 | 4 |
| N—(2-cyanoethyl)-carbanilic acid-(3-(3-cyclopropylureido)-phenyl)-ester | 4 | 4 | 4 | 4 |
| N—cyanomethyl-3-methyl-carbanilic acid-(3-(3-ethylureido)-phenyl)-ester | — | — | 4 | 4 |
| N—cyanomethylcarbanilic acid-(3-(3-propylureido)-phenyl)-ester | — | — | 4 | 4 |
| N—cyanomethylcarbanilic acid-(3-(3-cyclopropylureido)-phenyl)-ester | — | — | 4 | 4 |
| N—cyanomethylcarbanilic acid-(3-(3-butylureido)-phenyl-ester | 4 | 4 | 4 | 4 |
| N—cyanomethylcarbanilic acid-(3-(3-allylureido)-phenyl)-ester | 4 | 4 | 4 | 4 |
| N—cyanomethyl-3-methylcarbanilic acid-(3-(3,3-dimethylureido)-phenyl)-ester | 4 | 4 | 4 | 4 |
| N—cyanomethyl-3-methylcarbanilic acid-(3-(3-isopropylureido)-phenyl)-ester | — | — | 4 | 4 |
| N—cyanomethyl-3-methylcarbanilic acid-(3-(3-methylureido)-phenyl)-ester | — | — | 4 | 4 |
| N—cyanomethyl-3-methylcarbanilic acid-(3-(3-propylureido)-phenyl)-ester | — | — | 4 | 4 |
| 3-chloro-N—cyanomethyl-carbanilic acid-(3-(3,3-dimethylureido)-phenyl)-ester | 4 | 4 | 4 | 4 |
| N—cyanomethyl-3,4-dichlorocarbanilic acid-(3-(3,3-dimethylureido)-phenyl)-ester | — | — | 4 | 4 |
| N—cyanomethyl-3-chloro-carbanilic acid-(3-(3-ethylureido)-phenyl)-ester | — | — | 4 | 4 |
| N—cyanomethyl-3-methoxycarbanilic acid-(3-(3,3-dimethylureido)-phenyl)-ester | — | — | 4 | 4 |
| 3-chloro-N—cyanomethyl-carbanilic acid-(3-(3-propylureido)-phenyl)-ester | — | — | 4 | 4 |
| N—cyanomethyl-3-methylcarbanilic acid-(3-(3-allylureido)-phenyl)-ester | — | — | 4 | 4 |
| N—cyanomethyl-3-methoxycarbanilic acid-(3-(3-methylureido)-phenyl)-ester | — | — | 4 | 4 |
| N—cyanomethyl-3-methoxycarbanilic acid-(3-(3-propylureido)-phenyl)-ester | 4 | 4 | 4 | 4 |
| N—cyanomethyl-3-methoxycarbanilic acid-(3-(3-allylureido)-phenyl)-ester | — | — | 4 | 4 |
| 3-chloro-N—cyanomethyl-4-methylcarbanilic acid-(3-(3-methylureido)-phenyl)-ester | — | — | 4 | 4 |
| 3-chloro-N—cyanomethyl-4-methylcarbanilic acid-(3-(3,3-dimethylureido)-phenyl)-ester | — | — | 4 | 4 |
| N—cyanomethyl-3-methoxycarbanilic acid-(3-(3-ethylureido)-phenyl)-ester | — | — | 4 | 4 |
| N—(2-methoxyethyl)-3-methyl-carbanilic acid-(3-(3,3-dimethylureido)-phenyl)-ester | 4 | 4 | 4 | 4 |
| 3-chloro-N—cyanomethyl-4-methylcarbanilic acid-(3-(3-ethylureido)-phenyl)-ester | 4 | 4 | 4 | 4 |
| N—cyanomethyl-3,5-dimethylcarbanilic acid-(3-(3-methylureido)-phenyl)-ester | — | — | 4 | 4 |

TABLE I-continued

| Compound of the invention | Preemergence Sinapis | Preemergence Solanum | Postemergence Sinapis | Postemergence Solanum |
|---|---|---|---|---|
| N—cyanomethyl-4-methylthiocarbanilic acid-(3-(3-methylureido)-phenyl)-ester | — | — | 4 | 4 |
| N—cyanomethyl-3,5-dimethylcarbanilic acid-(3-(3,3-dimethylureido)-phenyl)-ester | 4 | 4 | 4 | 4 |
| N—cyanomethyl-4-methylthiocarbanilic acid-(3-(3,3-dimethylureido)-phenyl)-ester | — | — | 4 | 4 |
| N—cyanomethyl-3,5-dimethylcarbanilic acid-(3-(3-ethylureido)-phenyl)-ester | — | — | 4 | 4 |
| N—cyanomethyl-4-methylthiocarbanilic acid-(3-(3-ethylureido)-phenyl)-ester | — | — | 4 | 4 |
| N—cyanomethyl-3,5-dimethylcarbanilic acid-(3-(3-allylureido)-phenyl)-ester | — | — | 4 | 4 |
| N—cyanomethyl-4-methylthiocarbanilic acid-(3-(3-allylureido)-phenyl)-ester | — | — | 4 | 4 |
| N—cyanomethyl-3,4-dimethylcarbanilic acid-(3-(3-methylureido)-phenyl)-ester | — | — | 4 | 4 |
| N—cyanomethyl-3,4-dimethylcarbanilic acid-(3-(3-ethylureido)-phenyl)-ester | — | — | 4 | 4 |
| N—cyanomethyl-3,4-dimethylcarbanilic acid-(3-(3-allylureido)-phenyl)-ester | — | — | 4 | 4 |
| 3,4-dichloro-N—cyanomethylcarbanilic acid-(3-(3-ethylureido)-phenyl)-ester | — | — | 4 | 4 |
| N—(2-methoxyethyl)-3-methyl-carbanilic acid-(3-(3-methylureido)-phenyl)-ester | 4 | 4 | 4 | 4 |
| N—(2-methoxyethyl)-3-methyl-carbanilic acid-(3-(3-ethylureido)-phenyl)-ester | 4 | 4 | 4 | 4 |
| 3,5-dimethyl-N—(2-methoxyethyl)-carbanilic acid-(3-(3,3-dimethylureido)-phenyl)-ester | 4 | 4 | 4 | 4 |
| 3-chloro-N—cyanomethyl-carbanilic acid-(3-(3-allylureido)-phenyl)-ester | — | — | 4 | 4 |
| N—cyanomethyl-3,4-dimethylcarbanilic acid-(3-(3,3-dimethylureido)-phenyl)-ester | — | — | 4 | 4 |
| N—cyanomethyl-3,5-dichlorocarbanilic acid-(3-(3-methylureido)-phenyl)-ester | — | — | 4 | 4 |
| N—cyanomethyl-3,4-dichlorocarbanilic acid-(3-(3-methylureido)-phenyl)-ester | — | — | 4 | 4 |
| N—(2-methoxyethyl)-carbanilic acid-(3-(3,3-dimethylureido)-phenyl)-ester | 4 | 4 | 4 | 4 |
| N—cyanomethyl-3,5-dichlorocarbanilic acid-(3-(3,3-dimethylureido)-phenyl)-ester | — | — | 4 | 4 |
| N—(2-butoxyethyl)-carbanilic acid-[3-(3-methylureido)-phenyl]-ester | 4 | 4 | 4 | 4 |
| N—(2-butoxyethyl)-carbanilic acid-(3-(3-ethylureido)-phenyl)-ester | — | — | 4 | 4 |
| N—hexylcarbanilic acid-(3-(3-propylureido)-phenyl)-ester | — | — | 4 | 4 |
| N—(2-butoxyethyl)-carbanilic acid-(3-(3,3-dimethylureido)-phenyl)-ester | 4 | 4 | 4 | 4 |
| N—(2-butoxyethyl)-carbanilic acid-(3-(3-propylureido)-phenyl)-ester | — | — | 4 | 4 |
| N—(2-ethoxyethyl)-carbanilic acid-(3-(3,3-dimethylureido)-phenyl)-ester | 4 | 4 | 4 | 4 |
| N—(2-propoxyethyl)-carbanilic acid-(3-(3,3-dimethylureido)-phenyl)-ester | 4 | 4 | 4 | 4 |
| N—(2-cyanoethyl)-carbanilic acid-(3-(3-cyclohexylureido)-phenyl)-ester | — | — | 4 | 4 |

EXAMPLE 3

The compounds listed in the following Table II were applied in a hothouse in amounts of 1 kg of active agent per about 2.5 acres to the plants listed in the table at the incipient emergence. The compounds for this purpose were applied as dispersions in 500 liter of water per 2.5 acres in a uniform manner to the soil or to the plants.

The results were evaluated on a scale from 0 to 10, wherein 0=total destruction, and 10=no injury to the plant.

The results show that the compounds of the invention have a high selectivity as distinguished from the comparison compound.

TABLE II

| Compound of the invention | soybeans | peas | alfalfa | potatoes | maize | sorghum | rice | wheat | barley | Amaranthus | Chrysanthemum | Polygonum | Setaria |
|---|---|---|---|---|---|---|---|---|---|---|---|---|---|
| N—(2-cyanoethyl)-carbanilic acid-(3-(3,3-dimethyl-ureido)-phenyl)-ester | 10 | 10 | 10 | 10 | 10 | 10 | 10 | 10 | 10 | 0 | 0 | 0 | 0 |
| N—cyanomethyl-carbanilic acid-(3-(3,3-dimethyl-ureido)-phenyl)-ester | 10 | 10 | 10 | 10 | 10 | 10 | 10 | 10 | 10 | 0 | 0 | 0 | 0 |

TABLE II-continued

| Compound | | | | | | | | | | | | | |
|---|---|---|---|---|---|---|---|---|---|---|---|---|---|
| N—(2-methoxyethyl)-3-methylcarbanilic acid-(3-(3,3-dimethylureido)-phenyl)-ester Comparison compound (West German published application 1,518,815) | 10 | 10 | 10 | 10 | 10 | 10 | 10 | 10 | 10 | 0 | 0 | 0 | 0 |
| N—(3-(N—tert.-butylcarbamoyloxy)-phenyl)-N',N'—dimethyl-urea | 0 | 0 | 2 | 0 | 5 | 1 | 1 | 0 | 0 | 0 | 0 | 0 | 0 |
| Untreated | 10 | 10 | 10 | 10 | 10 | 10 | 10 | 10 | 10 | 10 | 10 | 10 | 10 |

| Compound of the invention | Poa | Alope-curus | Ag-ro-stis | Cen-tau-rea | Lam-ium | Matri-caria | Sene-cio | Stel-laria | Spo-moca | Datura | Pha-celia | Cheir-anthus | Eschult-zin | Sela-num |
|---|---|---|---|---|---|---|---|---|---|---|---|---|---|---|
| N—(2-cyanoethyl)-carbanilic acid-(3-(3,3-dimethyl-ureido)-phenyl)-ester | 0 | 0 | 0 | 0 | 0 | 0 | 0 | 0 | 0 | 0 | 0 | 0 | 0 | 0 |
| N—cyanomethyl-carbanilic acid-(3-(3,3-dimethyl-ureido)-phenyl)-ester | 0 | 0 | 0 | 0 | 0 | 0 | 0 | 0 | 0 | 0 | 0 | 0 | 0 | 0 |
| N—(2-methoxyethyl)-3-methylcarbanilic acid-(3-(3,3-dimethylureido)-phenyl)-ester Comparison compound (West German published application 1,518,815) | 0 | 0 | 0 | 0 | 0 | 0 | 0 | 0 | 0 | 0 | 0 | 0 | 0 | 0 |
| N—(3-(N—tert.-butylcarbamoyloxy)-phenyl)-N',N'—dimethyl-urea | 0 | 0 | 0 | 0 | 0 | 0 | 0 | 0 | 0 | 0 | 0 | 0 | 0 | 0 |
| Untreated | | 10 | 10 | 10 | 10 | | 10 | 10 | 10 | 10 | 10 | 10 | 10 | 10 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Carbanilic acid-(3-ureido-phenyl)-ester of the formula

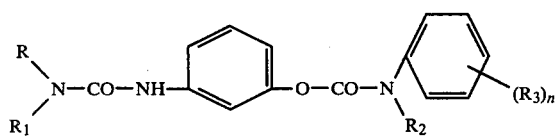

in which R is an aliphatic, straight chain, branched or cyclic, saturated or unsaturated hydrocarbon residue of 1 to 6 carbons, $R_1$ is hydrogen or methyl, $R_2$ is cyanoalkyl or alkoxyalkyl, $R_3$ is the same or different if more than one and is hydrogen, alkyl, alkoxy, alkylthio or halogen and n is 1 or 2.

2. The carbanilic acid ester of claim 1 in which R is propenyl, propinyl, cyclopropyl or cyclohexyl, $R_1$ is hydrogen or methyl, $R_2$ is cyanomethyl, 2-cyanoethyl or 2-methoxyethyl, 2,2-dimethoxyethyl, 2-ethoxyethyl, 2-propoxyethyl or 2-butoxyethyl, and $R_3$ is hydrogen, methyl, methoxy, methylthio and/or chlorine.

3. The compound of claim 1 which is N-(2-cyanoethyl)-carbanilic acid-[3-(3-methylureido)-phenyl]-ester.

4. The compound of claim 1 which is N-(2-cyanoethyl)-carbanilic acid-[3-(3-cyclopropylureido)-phenyl]-ester.

5. The compound of claim 1 which is N-(2-cyanoethyl)-carbanilic acid-[3-(3,3-dimethylureido)-phenyl]-ester.

6. The compound of claim 1 which is N-(2-cyanoethyl)-carbanilic acid-[3-(3-propylureido)-phenyl]-ester.

7. The compound of claim 1 which is N-(2-cyanoethyl)-carbanilic acid-[3-[3-(2-propenyl)-ureido]-phenyl]-ester.

8. The compound of claim 1 which is N-(2-cyanoethyl)-carbanilic acid-[3-(3-butylureido)-phenyl]-ester.

9. The compound of claim 1 which is N-(2-cyanoethyl)-carbanilic acid-[3-(3-isopropylureido)-phenyl]-ester.

10. The compound of claim 1 which is N-(2-cyanoethyl)-3-methylcarbanilic acid-[3-(3-isopropylureido)-phenyl]-ester.

* * * * *